United States Patent
Gabizon et al.

(10) Patent No.: US 6,787,132 B1
(45) Date of Patent: Sep. 7, 2004

(54) COMBINED CHEMO-IMMUNOTHERAPY WITH LIPOSOMAL DRUGS AND CYTOKINES

(75) Inventors: Alberto A. Gabizon, Jerusalem (IL); Eliezer Kedar, Jerusalem (IL); Yechezkel Barenholz, Jerusalem (IL)

(73) Assignees: Yissum Research Development Company of the Hebrew University of Jerusalem, Jerusalem (IL); Hadasit Medical Research Services and Development, Ltd., Jerusalem (IL)

( * ) Notice: Subject to any disclaimer, the term of this patent is extended or adjusted under 35 U.S.C. 154(b) by 0 days.

(21) Appl. No.: 09/555,674

(22) PCT Filed: Dec. 1, 1998

(86) PCT No.: PCT/IL98/00586

§ 371 (c)(1), (2), (4) Date: Aug. 3, 2000

(87) PCT Pub. No.: WO99/27908

PCT Pub. Date: Jun. 10, 1999

Related U.S. Application Data

(60) Provisional application No. 60/067,697, filed on Dec. 4, 1997.

(51) Int. Cl.[7] ................. A61K 38/19; A61K 38/20; A61K 38/21; C07B 265/34

(52) U.S. Cl. ............. 424/85.2; 424/85.1; 424/85.6; 424/85.7; 544/100

(58) Field of Search ............... 424/85.1, 85.2, 424/85.4, 85.5, 85.6, 85.7; 530/351; 544/100

(56) References Cited

U.S. PATENT DOCUMENTS

| | | | |
|---|---|---|---|
| 4,235,871 A | | 11/1980 | Papahadjopoulos et al. |
| 4,426,330 A | | 1/1984 | Sears |
| 4,534,899 A | | 8/1985 | Sears |
| 5,013,556 A | * | 5/1991 | Woodle et al. ............ 424/450 |
| 5,316,763 A | * | 5/1994 | Ochoa et al. |
| 5,316,771 A | | 5/1994 | Barenholz et al. |
| 5,409,698 A | * | 4/1995 | Anderson et al. |
| 5,552,156 A | * | 9/1996 | Burke ....................... 424/450 |

FOREIGN PATENT DOCUMENTS

| | | |
|---|---|---|
| DE | 44 30 593 | 2/1996 |
| EP | 0 433 765 | 6/1991 |
| EP | 0 546 951 | 6/1993 |
| WO | WO 85/00968 | 3/1985 |
| WO | WO 90/13293 | * 11/1990 |

OTHER PUBLICATIONS ten Hagen et al., Proceedings of the American Association for Cancer Research, vol. 38 abstract #1734, Mar. 1997.*
Chow et al., Proceedings of the American Association for Cancer Research, vol. 38 abstract #1734, Mar. 1997.*
Poirot et al., Proceedings of the American Association for Cancer Research, vol. 37 abstract #2039, Mar. 1996.*
Kedar et al., J. Immunotherapy, vol. 20. 20 No.5 p. 415 (Sep. 1997).*
Kedar et al., (1993) Biological Response to Modifiers, 2nd International congress p. 55.*
Kedar et al., (1994) J. Immunotherapy, vol. 16 pp. 115–124.*

(List continued on next page.)

Primary Examiner—Jon P. Weber
(74) Attorney, Agent, or Firm—Browdy and Neimark

(57) ABSTRACT

A method of antitumor therapy is described in which administration of a chemotherapeutic drug, encapsulated in liposomes, is supplemented by administration of an immunostimulating cytokine. The cytokine is preferably also encapsulated in liposomes. In tumor models for lung and colon carcinomas, this method produced a significantly greater therapeutic effect, as evidenced by survival rate and tumor size, than a combination of the effects produced by the free or liposome-encapsulated components administered individually.

20 Claims, 2 Drawing Sheets

OTHER PUBLICATIONS

D.P. Curran et al., "Cascade Radical Reactions of Isonitriles: A Second–Generation Synthesis of (20S)–Camptothecin, Topotecan, Irinotecan, and Gl–147211C", *Angew. Chem. Int. Ed. Engl.*, 1995, vol. 34, No. 23/24, pp. 2683–4.

*Liposomes And Immunobiology: Proceedings Of A National Symposium Held Mar. 14–15, 1980, In Houston, Texas*, Ed. B.H. Tom and H.R. Six, Elsevier Press, 1980, pp. 93–119.

Abstract for Papahadjopoulos et al., "Sterically Stabalized Liposomes: Improvements in Pharmacokinetics and Antitumor Therapeutic Efficacy", *Proc. Natl. Acad. Sci. USA*, Dec. 15, 1991; 88(24):11460–4.

Abstract for JP 63048225, "Carcinostatic contg. interferon–alpha used as remedy for pharynx cancer with bleomycin", Green Cross Corp, Feb. 29, 1988.

Hudson et al., "In Vitro and In Vivo Effect of Adriamycin Therapy on Monocyte Activation by Liposome–encapsulated Immunomodulators", *Cancer Research*, Sep. 15, 1988, vol. 48, pp. 5256–5263.

Eli Kedar et al., "Delivery of Cytokines by Liposomes. I. Preparation and Characterization of Interleukin–2 Encapsulated in Long–Circulating Sterically Stabilized Liposomes", *Journal of Immunotherapy*, 1994, vol. 16, pp. 47–59.

*Stealth Liposomes*, edited by Danilo LASIC and Frank Martin, London: CRC Press, 1995, Introduction; pp. 279–280.

D. Papahadjopoulos et al., "Sterically Stabilized Liposomes: Improvements in Pharmacokinetics and Antitumor Therapeutic Efficacy", *Proc. Natl. Acad. Sci. USA*, Dec. 1991, vol. 88, pp. 11460–11464.

Saxton et al., "Adoptive Transfer of Anti–CD3–Activated $CD4^+T$ Cells Plus Cyclophosphamide and Liposome–Encapsulated Interleukin–2 Cure Murine MC–38 and 3LL Tumors and Establish Tumor–Specific Immunity", *Blood*, Apr. 1, 1997, vol. 89, No. 7, pp. 2529–2536.

Adler et al., "Allogenic Human Liposomal Melanoma Vaccine with or without IL–2 in Metastic Melanoma Patients: Clinical and Immunological Effects", *Cancer Biotherapy*, 1995, vol. 10, No. 4, pp. 293–306.

Szoka et al., "Comparative Properties and Methods of Preparation of Lipid Vesicles (Liposomes)", *Ann. Rev. Biophys. Biogeng.*, 1980, vol. 9, pp. 467–508.

Tirosh et al., "Novel Synthetic Phospholipid Protects Lipid Bilayers Against Oxidation Damage: Role of Hydration Layer and Bound Water", *Chem. Soc., Perk Trans. 2*, 1997, pp. 383–389.

* cited by examiner

COMBINED CHEMO-IMMUNOTHERAPY WITH LIPOSOMAL DRUGS AND CYTOKINES

CROSS-REFERENCE TO RELATED APPLICATIONS

This application is a 371 of PCT/IL98/00586, filed Dec. 1, 1998, which claims priority under 35 USC 119(e) to U.S. Provisional application No. 60/067,697 filed Dec. 4, 1997.

FIELD OF THE INVENTION

The present invention relates to a method and composition for antitumor therapy, and more particularly to combination therapy using a chemotherapeutic drug and an immunostimulating cytokine. Sequential administration of these two components, both encapsulated in liposomes, is shown to have a significant antitumor effect as compared to administration of the individual components, in free form or in liposomes.

References

Adler, A. et al., *Cancer Biotherapy* 10:293–306 (1995).

Curran, D. P. et al., *Angew. Chem. Intl. Ed. Eng.* 34(23/24):2683–4 (1996).

Gabizon, A. et al., *Adv. Drug Delivery Reviews* 24(2–3):337–344 (1997).

Kedar, E. et al., *J. Immunotherapy* 16:47–59 (1994).

Lasic, D. and Martin F., Eds., STEALTH LIPOSOMES CRC Press, Boca Raton, Fla. (1995).

Papahadjopoulos, D. et al., *Proc. Natl. Acad. Sci. USA* 88:11460–11464 (1991).

Sears, B. D., U.S. Pat. No. 4,426,330 (1984).

Sears, B. D., U.S. Pat. No. 4,534,899 (1985a).

Szoka, F., Jr. et al., U.S. Pat. No. 4,235,871 (1980b).

Szoka, F., Jr. et al., *Ann. Re. Biophys. Bioeng.* 9:467 (1980).

Tirosh, O. et al., *J. Chem. Soc. Perk. Trans. II* 2:383–389 (1997).

Woodle, M. C. et al., U.S. Pat. No. 5,013,556 (1991).

BACKGROUND OF THE INVENTION

Despite prolific research in the area of cancer chemotherapy, such treatment remains far from satisfactory. The inability of chemotherapeutic drugs to reach the tumor site, intrinsic and acquired cross-resistance to multiple chemotherapeutic agents, and, especially, the high toxicity of many of these agents all contribute to treatment failures.

The use of immunostimulating cytokines, such as IL-2 and interferon-α, has proven to be effective in treatment of a proportion of patients with malignancies such as melanoma and renal cell carcinoma, both alone and in combination with other therapeutic agents. However, major problems limit their wide clinical use, including rapid plasma clearance, biodistribution to nonrelevant tissues, and high toxicity. Furthermore, their efficacy has been low in treatment of the most common tumors, e.g. colorectal, mammary, prostate, and lung carcinomas.

SUMMARY OF THE INVENTION

The present invention includes, in one aspect, a method of antitumor therapy, which comprises administering to a subject in need of such treatment, a therapeutically effective amount of a combination of a chemotherapeutic drug and an immunostimulating cytokine, both encapsulated in liposomes. In another aspect, the invention provides a composition for use in antitumor therapy, which comprises such a combination of a chemotherapeutic drug and an immunostimulating cytokine, both encapsulated in liposomes. Administration of the combination produces a greater therapeutic effect than a combination of the effects produced by the liposome-encapsulated components administered individually.

The invention also includes a method of antitumor therapy in which a chemotherapeutic drug, encapsulated in liposomes, is administered in combination with a cytokine, which may or may not be encapsulated in liposomes. In this method, the drug is encapsulated in liposomes which contain about 1–10 mole percent of a lipid having a polar head group derivatized with a polyethylene glycol (PEG) chain which has a molecular weight of between 750 and 10,000 daltons. The therapeutic effect of this combination is greater than a combination of the effects produced by the liposome-encapsulated drug and the cytokine administered individually.

In all cases, administration of the cytokine preferably follows administration of the liposome-encapsulated drug.

The chemotherapeutic drug is preferably selected from cis-platin, a chemotherapeutic anthraquinone, and a topoisomerase I inhibitor, such as camptothecin or a camptothecin analog. More preferably, the drug is adriamycin (doxorubicin), in which case the liposome-encapsulated form of the drug is preferably DOXIL®, a polyethylene glycol-coated liposomal doxorubicin.

The immunostimulating cytokine is preferably selected from the group consisting of interleukin-2 (IL-2), IL-12, IL-15, IL-18, IFN-γ, IFN-α, IFN-β, TNF-α, G-CSF, and GM-CSF. More preferably, the cytokine is IL-2.

The encapsulating liposomes employed in the composition and method preferably contain at least one lipid selected from dimyristoyl phosphatidyl choline (DMPC), dimyristoyl phosphatidyl glycerol (DMPG), 1,2-distearoyl-3-trimethylammonium propane (DSTAP), phosphatidyl choline, phosphatidyl ethanolamine, and cholesterol.

The liposomes may be small unilamellar vesicles (SUV), defined as having a mean diameter of approximately 20 to 100 nm, or large unilamellar vesicles (LUV), defined as having a mean diameter of approximately 100 to 200 nm. Such liposomes preferably contain about 1–10 mole percent of a lipid having a polar head group derivatized with a polyethylene glycol (PEG) chain which has a molecular weight of between 750 and 10,000 daltons.

Alternatively, the liposomes may be large multilamellar vesicles (MLV) having a mean diameter of approximately 250 to 2000 nm. The MLV may also contain a PEG-derivatized lipid as described above.

In preferred embodiments, the chemotherapeutic drug is encapsulated in vesicles having a mean diameter of approximately 50 to 120 nm, and containing about 1–10 mole percent of a lipid having a polar head group derivatized with a polyethylene glycol (PEG) chain as described above. In another preferred embodiment, the cytokine is encapsulated in liposomes containing dimyristoyl phosphatidyl choline (DMPC) plus 0 to 50 mole percent of at least one lipid selected from dimyristoyl phosphatidyl glycerol (DMPG) and 1,2-distearoyl-3-trimethylammonium propane (DSTAP).

These and other objects and features of the invention will become more fully apparent when the following detailed

DETAILED DESCRIPTION OF THE INVENTION

I. Definitions

Figure 1:
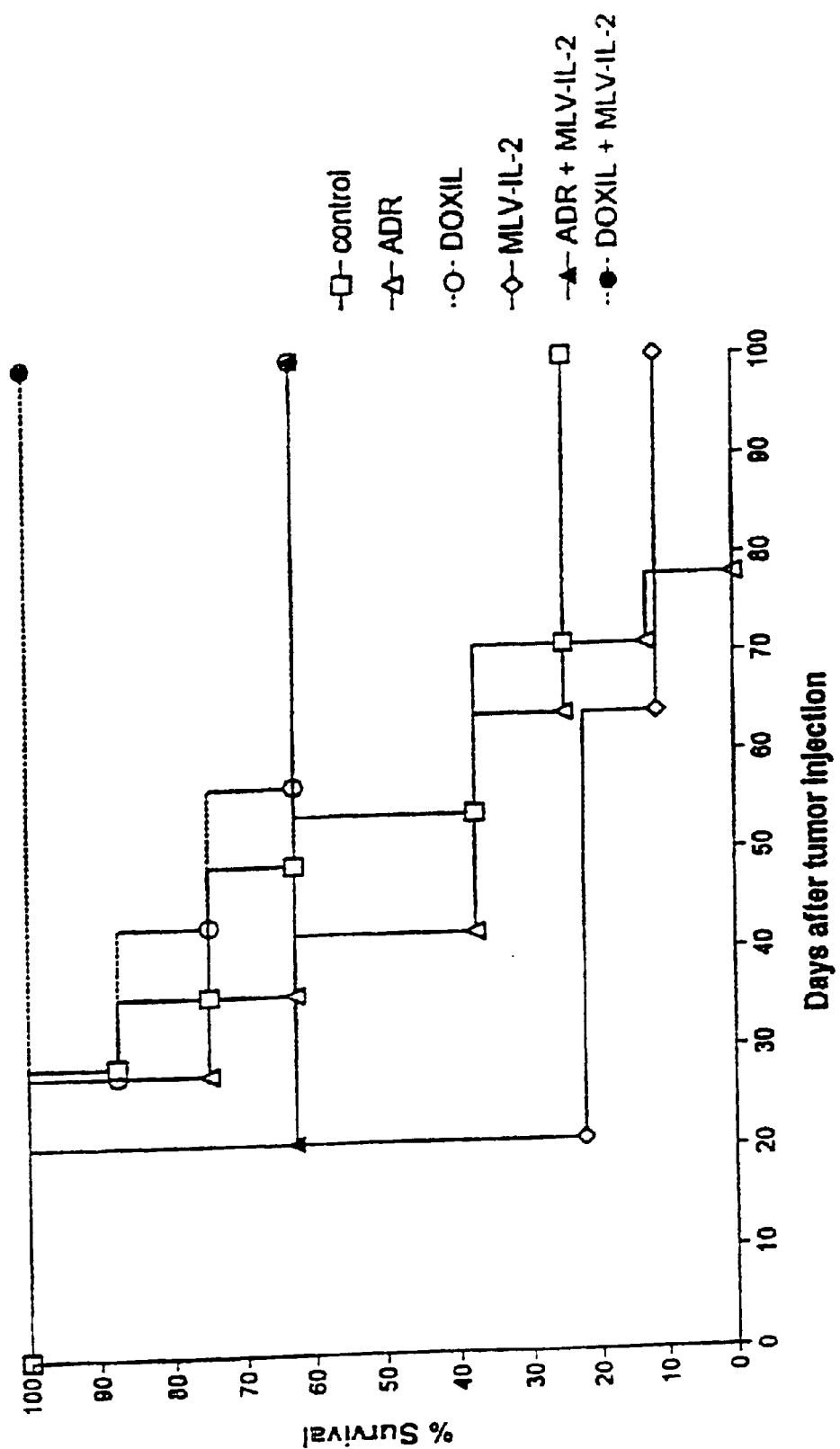
FIG. 1 shows the survival rate of BALB/c mice injected intraperitoneally with $5 \times 10^5$ M109 tumor cells (lung adenocarcinoma) and subsequently treated with free adriamycin or DOXIL®, respectively, alone or in combination with intraperitoneal IL-2 in DMPC/DMPG MLV liposomes, or with liposomal IL-2 alone.

The terms below have the following meanings unless indicated otherwise.

"Vesicle-forming lipids" refers to amphipathic lipids which have hydrophobic and polar head group moieties, and which (a) can form bilayer vesicles in water, as exemplified by phospholipids, or (b) can be stably incorporated into lipid bilayers, with the hydrophobic moiety in contact with the interior, hydrophobic region of the bilayer membrane, and the polar head group moiety oriented toward the exterior, polar surface of the membrane.

The vesicle-forming lipids of this type typically include one or two hydrophobic acyl hydrocarbon chains or a steroid group, and may contain a chemically reactive group, such as an amine, acid, ester, aldehyde or alcohol, at the polar head group. Included in this class are the phospholipids, where the two hydrocarbon chains are typically between about 14–22 carbon atoms in length, and have varying degrees of unsaturation. Representative examples are phosphatidyl choline (PC), phosphatidyl ethanolamine (PE), phosphatidic acid (PA), phosphatidyl inositol (PI), sphingomyelin (SM), negatively charged lipids such as dimyristoyl phosphatidyl glycerol (DMPG), and positively charged lipids such as 1,2-distearoyl-3-trimethylammonium propane (DSTAP). The liposomes may also contain sterols, such as cholesterol, which do not form liposomes themselves but can be incorporated into, and may stabilize, liposomes containing lipids such as those described above.

A "Cetus unit" (CU) is equal to six International Units (IU) of Immunological Activity, the international reference standard of a biological preparation of interleukin-2 (IL-2). The term "unit" used herein in reference to cytokine levels refers to Cetus units.

II. Liposomal Compositions

A. Lipid Components

Various vesicle-forming lipids, as defined above, may be used in the present liposomal compositions, according to methods well known in the art. Preferred lipids for the current invention allow long-term storage of the liposome-entrapped agents and effective release of these components upon administration. Representative lipids include, but are not limited to, dimyristoyl phosphatidylcholine (DMPC), dimyristoyl phosphatidylglycerol (DMPG), cholesterol, egg phosphatidylcholine (egg PC), phosphatidyl ethanolamine (PE), distearoyl phosphatidyl ethanol-amine (DSPE), phosphatidyl inositol (PI), 1,2-distearoyl-3-trimethylammonium propane (DSTAP), 1,2-dimyristoyl-3-trimethylammonium propane (DMTAP), and combinations thereof.

The vesicle-forming lipids, preferably those making up SUV's, may contain about 1–10 mole percent of a lipid having a polar head group, typically a phosphate containing head group, derivatized with a polyethylene glycol (PEG) chain which has a molecular weight of between 750 and 10,000 daltons. The rate of clearance of liposomes from circulation is typically reduced by employing such PEG-derivatized, or "PEGylated", lipids. PEG coating is believed to inhibit nonspecific adsorption of serum proteins, thereby preventing nonspecific recognition of liposomes by macrophages (Papahadjopoulos, et al., 1991). Another advantage of these long-circulating liposomes is their good extravasation capacity and high accumulation in tumors (Lasic and Martin, 1995; Gabizon, et al., 1997). They are also referred to as sterically stabilized liposomes, SSL, or STEALTH® liposomes.

The preparation of such lipids is described in, for example, Woodle, et al., 1991; Sears (1984, 1985); Tirosh et al. (1997) or copending and co-owned application having U.S. Ser. No. 08/570,440. The PEG chain may be linked directly to the phosphatidic acid head group of a phospholipid. Various other linkages are possible; for example, lipids containing a phosphatidyl ethanolamine (PE) or other amino head group may be conveniently coupled to activated PEG chains via reaction with brominated PEG. PEG-modified lipids are also commercially available, e.g. from Sequus Corporation, Menlo Park, Calif.

B. Preparation of Liposomes and Liposomal Compositions

Liposomes may be prepared by a variety of techniques, such as those detailed in Szoka et al. (1980b). To form multilamellar vesicles (MLV's), a mixture of vesicle-forming lipids dissolved in a suitable solvent is evaporated in a vessel to form a thin film, which is then hydrated by an aqueous median to form MLV's, typically with sizes between about 0.1 to 10 microns. Tert-butanol is a preferred solvent for the process. The MLV's may then be downsized to a desired size range by extruding the aqueous suspension through a polycarbonate membrane having a selected uniform pore size, typically 0.05 to 1.0 microns.

Preparations of MLV's or REV's (described below) may be treated, e.g. by extrusion, sonication or high pressure homogenization, to produce unilamellar vesicles. Small unilamellar vesicles (SUV's) are characterized by sizes in the 30–100 nm range, while large unilamellar vesicles (LUV's) are defined as those having mean diameters of about 100–200 nm. SUV's may also be formed directly by high pressure homogenization of an aqueous dispersion of lipids.

Various methods are available for encapsulating other agents in liposomes. Preparation of SSL-encapsulated IL-2 is described in Kedar et al. (1994). In this procedure, generally, the lipid components, including a PEG-substituted lipid, are dissolved in t-butanol. The solution is sonicated, and IL-2 is added with further sonication. The mixture is lyophilized and rehydrated, forming MLV's, which can then be downsized by high pressure homogenization or by successive extrusion through polycarbonate filters. These downsizing methods gave vesicles having diameters of 50–80 nm and about 200 nm, respectively. The procedure achieved approximately 80–90% encapsulation of the IL-2.

In the reverse phase evaporation method (Szoka, et al., 1980a) a nonaqueous solution of vesicle-forming lipids is dispersed with a smaller volume of an aqueous medium to form a water-in-oil emulsion. The agent to be incorporated is included either in the lipid solution, in the case of a lipophilic agent, or in the aqueous medium, in the case of a water-soluble agent. After removal of the lipid solvent, the resulting gel is converted to liposomes. These reverse phase evaporation vesicles (REVs) have typical average sizes between about 0.2–4 microns and are predominantly oligolamellar, that is, containing one or a few lipid bilayer shells. The REVs may be sized by extrusion, if desired, to give oligolamellar vesicles having a maximum selected size between about 0.05 to 1.5 microns.

Other methods for adding additional components to liposomal compositions include colyo-philization with other components and redispersion of the resulting solid to form MLV's. In a method described by Adler, et al. (1995), an aqueous solution of the agent to be encapsulated is added to a t-butanol solution of lipids. The mixture is sonicated and lyophilized, and the resulting powder is rehydrated.

Liposome compositions containing an entrapped agent may be treated after final sizing, if necessary, to remove free (non-entrapped) agent. Conventional separation techniques, such as centrifugation, diafiltration, and molecular-sieve chromatography are suitable for this purpose. The composition may also be sterilized by filtration through a conventional 0.22 or 0.45 micron depth filter.

To form the compositions of the current invention, the concentration of drug and/or cytokine in the liposomes is preferably effective to give a protein/lipid weight ratio between about 1:100 and 1:1000.

Stabilizers may also be added to the liposomal compositions. For example, addition of a metal chelator such as Desferal™ or diethylenetriamine pentaacetic acid (DTPA) to the lyophilization medium, at a concentration of 100 µM, has been shown to reduce activity loss of entrapped IL-2 during liposome preparation and storage at 4° C. Antioxidants such as BHT or Vitamin E may also be included.

For long term storage, the compositions may be stored as the dry lyophilized powder, which is stable for at least a year at 4° C., and hydrated to form an aqueous suspension before use.

III. Combined Chemotherapy/Cytokine Therapy

A. Formulations

Cytokines useful for enhancing antitumor activity of chemotherapeutic drugs include IL-2, IL-12, IL-15, IL-18, IFN-γ, IFN-α, IFN-β, TNF-α, G-CSF, and GM-CSF. A preferred cytokine for the present invention is IL-2 (interleukin 2), which acts as a growth and maturation factor for T-lymphocytes.

A variety of liposomal formulations may be used for encapsulation of the cytokine. These include MLV, LUV or SUV, as defined above, as well as OLV (oligolamellar vesicles) and MVV (multivesicular vesicles), composed of vesicle-forming lipids such as those described above. Combinations of lipids are generally most effective (see, for example, Kedar et al., 1994). One preferred type of formulation employs SUV or LUV, having a mean diameter of approximately 50 to 120 nm, containing about 1–10 mole percent of a lipid having a polar head group derivatized with a polyethylene glycol (PEG) chain (also referred to as a PEGylated lipid). Formulation A below is one example. Other preferred formulations employ dimyristoyl phosphatidyl choline (DMPC) and, optionally, up to 50 mole percent of at least one lipid selected from dimyristoyl phosphatidyl glycerol (DMPG) and 1,2-distearoyl-3-trimethylammonium propane (DSTAP). In these formulations, the proportion of DMPG and/or DSTAP is more preferably 5–25 mole percent. Formulation B below is one example. In all cases, small quantities (up to about one mole percent) of stabilizers such as tocopherol or Desferal™ may be included.

For the experiments described below, liposomal IL-2 was prepared in two formulations, using IL-2 obtained from Chiron Corporation (Emeryville, Calif.), according to known methods such as those described above. Formulation A employed sterically stabilized (SSL) small unilamellar vesicles (SUV) composed of $^{2000}$PEG-DSPE (N-carbamyl-(polyethylene glycol methyl ether)-1,2-distearoyl-sn-glycero-3-phosphoethanolamine triethylammonium salt, provided by Sequus Corporation), egg phosphatidyl choline, and cholesterol in a molar ratio of about 5:55:40. The vesicles were about 50–70 nm in diameter. Encapsulation efficiency of IL-2 was greater than 80%, based on an in vitro IL-2 bioassay (i.e., >80% of the initial amount of added IL-2 became encapsulated in liposomes).

Formulation B employed multilamellar vesicles (MLV) composed of DMPC-DMPG (dimyristoyl phosphatidyl choline—dimyristoyl phosphatidyl glycerol) in a 9:1 molar ratio. The vesicles were approximately 500–1500 nm in size, and the encapsulation efficiency was approximately >90%. This high efficiency of encapsulation was achieved at a lipid:IL-2 ratio (wt:wt) of 1000:1 for DMPC alone, and 100:1 for DMPC containing DMPG or DSTAP.

The chemotherapeutic drug is preferably encapsulated in liposomes having about 1–10 mole percent of a PEGylated lipid, as described above. For example, DOXIL®, a stable formulation of adriamycin in STEALTH® liposomes, is available from SEQUUS Pharmaceuticals, Inc. (Menlo Park, Calif.). Free adriamycin is available, e.g., from Cetus Oncology Corp. (Emeryville, Calif.) as a formulation of doxorubicin hydrochloride and lactose.

Other chemotherapeutic drugs which are also preferred for the present method include other arthraquinones, such as epirubicin, daunorubicin, and mitoxanthrone, and cis-platin. Also contemplated are topoisomerase I inhibitors such as camptothecin and its analogs, e.g. topotecan and irinotecan, also designated CPT-11. Camptothecin is isolated from the stem wood of the Chinese tree *Camptotheca aciminata*; preparation of the above noted analogs has been described by, e.g., Curran et al. (1996).

B. Liposomal Adriamycin—Liposomal IL-2

The effect of adriamycin, used alone or in combination with interleukin-2 (IL-2), where each component was in free or liposome-encapsulated form, on the survival rate of BALB/c mice infected with tumor cells, was tested as described below.

B1. Lung Adenocarcinoma Model: IL-2 in MLV. Six groups of BALB/c mice were injected intraperitoneally with $5\times10^5$ M109 tumor cells (day 0). Free adriamycin or DOXIL®, respectively, were administered intravenously on day 7 at a dose of 8 mg/kg, and intraperitoneal cytokine treatment was initiated 3 days later. Liposomal IL-2 (formulation B; MLV DMPC/DMPG (9:1 mole ratio) liposomes containing IL-2) was given once daily (50,000 CU/mouse) on days 10, 13 and 16. Control groups received no treatment or received the IL-2 treatment alone.

Each group, consisting of 8–9 mice, was inspected for survival up to 100 days after tumor inoculation. Table I shows the number of survivors at the end of the experiment and the median survival time obtained; FIG. 1 shows the survival curves for all groups.

TABLE I

| GROUP | TREATMENT | NUMBER OF SURVIVING MICE/TOTAL | MEDIAN SURVIVAL (DAYS) |
|---|---|---|---|
| 1 | Control | 2/8 | 54 |
| 2 | ADR | 0/8 | 42 |
| 3 | ADR + MLV-IL-2 | 5/8 | >100 |
| 4 | DOXIL ® | 5/8 | >100 |
| 5 | DOXIL ® + MLV-IL-2 | 8/8 | >100 |
| 6 | MLV-IL-2 | 1/9 | 21 |

As Table I shows, adriamycin (ADR) in combination with MLV-IL-2 (liposomal IL-2, formulation B) was much more effective than either adriamycin alone or liposomal IL-2 alone, both of which showed lower survival rates than the control. When liposomal adriamycin (DOXIL®) was administered alone, or when non-liposomal adriamycin was combined with liposomal IL-2, five of eight mice survived for the duration of the test.

The best result, i.e. survival of all subjects for 100 days or more, was observed for the combination of liposomal ADR (DOXIL®) with liposomal IL-2. In terms of number of surviving subjects, the effect of the combination treatment was greater than a combination of the effects of the individual treatments.

B2. Metastatic Lung Adenocarcinoma Model: IL-2 in MLV (Formulation B) and PEG-Derivatized SUV (SSL). In this experiment, BALB/c mice were injected intravenously with $5 \times 10^5$ M109 tumor cells (day 0). Free adriamycin or DOXIL®, respectively, were administered intravenously on day 7 (8 mg/kg), followed 3 days later by intravenous cytokine treatment. Liposomal IL-2 (Formulation A; PEGylated SUV containing IL-2) was given once daily (50,000 CU/mouse) on days 11, 14 and 17. Control groups received no treatment or received the IL-2 treatment alone.

Figure 2:
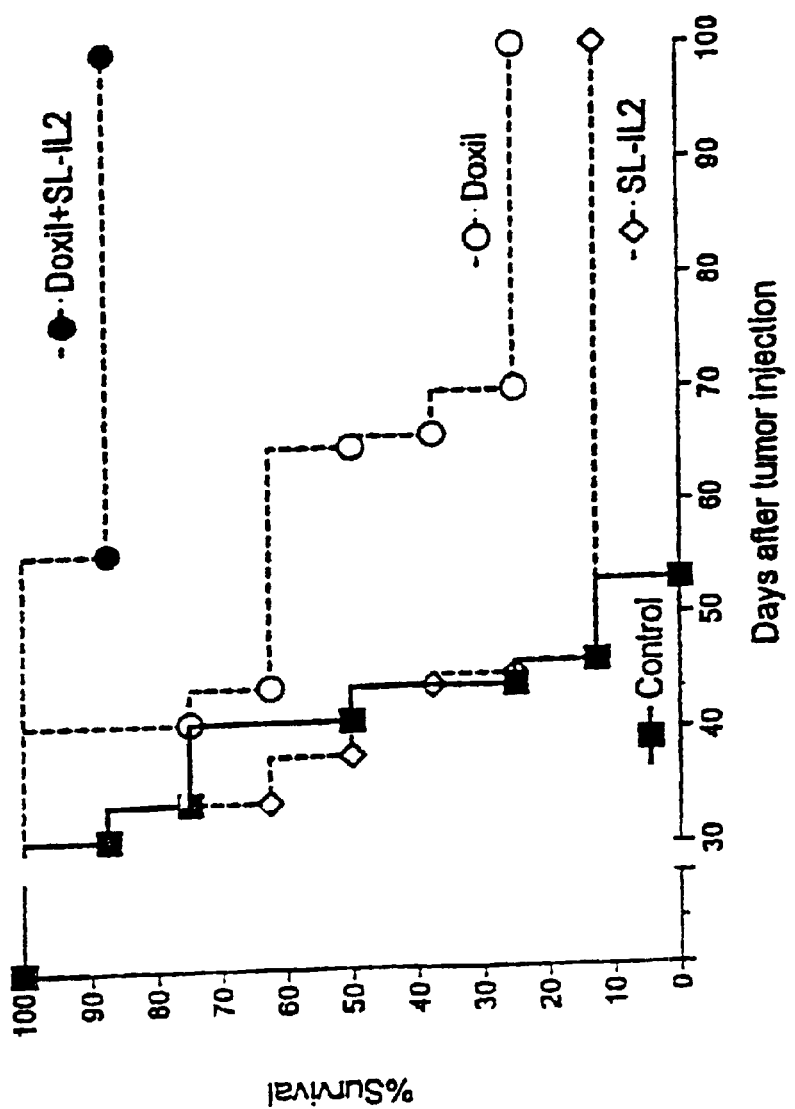
FIG. 2 shows the survival rate of BALB/c mice injected intravenously with $5 \times 10^5$ M109 tumor cells and subsequently treated with DOXIL® (at day 7), alone or in combination with intravenous IL-2 in STEALTH® PEGylated SUV liposomes (at days 11, 14, and 17), or with liposomal IL-2 alone (at days 11, 14, and 17).

Each group, consisting of 8–9 mice, was inspected for survival up to 100 days after tumor inoculation. Results are shown in Table II and FIG. 2.

TABLE II

| GROUP | TREATMENT | NUMBER OF SURVIVING MICE/TOTAL | MEDIAN SURVIVAL (DAYS) |
|---|---|---|---|
| 1 | Control | 0/8 | 43 |
| 2 | ADR | 2/8 | 56 |
| 3 | DOXIL ® | 1/8 | 66 |
| 4 | SSL-IL-2 | 0/8 | 41 |
| 5 | DOXIL ® + SSL-IL-2 | 7/9 | >100 |

As a comparison of groups 3–5 shows, the combined treatment with DOXIL® and liposomal IL-2 was significantly more effective than treatment with either liposomal component alone, particularly in terms of the number of subjects surviving for the duration of the test, i.e. 100 days or more (7 out of 9 compared to 0–1 out of 8). In this aspect, the combined treatment was significantly more effective than a combination of the effects derived from the individual therapies.

In a second, more extensive study, nine groups of BALB/c mice were injected intraperitoneally with $5 \times 10^5$ M109 tumor cells. Free adriamycin or DOXIL® (8 mg/kg) were administered intraperitoneally 7 days later, followed 3 days later by intravenous cytokine treatment. The cytokine, given once daily (50,000 CU/mouse) on days 10, 13 and 16, consisted of free IL-2, IL-2 in Formulation A (Stealth® PEGylated SUV), or IL-2 in Formulation B (9:1 molar DMPC/DMPG MLV).

Each group, consisting of 8 mice, and an untreated control group of 11 mice, were inspected for survival up to 120 days after tumor inoculation. Results are shown in Table III.

TABLE III

| GROUP | TREATMENT | NUMBER OF TUMOR FREE MICE/TOTAL | MEDIAN SURVIVAL (DAYS) |
|---|---|---|---|
| 1 | Control | 3/11 | 69 |
| 2 | ADR | 4/8 | 100 |
| 3 | ADR/free IL-2 | 3/8 | 53 |
| 4 | ADR/MLV-IL-2 | 4/8 | 92 |
| 5 | ADR/SSL-IL-2 | 3/8 | 72 |
| 6 | DOXIL ® | 4/8 | 102 |
| 7 | DOXIL ®/free IL-2 | 5/8 | >120 |
| 8 | DOXIL ®/MLV-IL-2 | 7/8 | >120 |
| 9 | DOXIL ®/SSL-IL-2 | 5/8 | >120 |

In this study, administration of free ADR and IL-2 showed little or no benefit over free ADR alone (groups 2–5). However, combinations of either free or liposomal IL-2 with the chemotherapeutic drug in liposomes (DOXIL®) showed clear benefits over administration of the drug alone (groups 6–9). Overall, the groups (8 and 9) treated with a combination of both components in liposomes showed superior results. Group 8, in particular, showed a high survival rate and almost a complete absence of tumors.

B3. Subcutaneous colon carcinoma model: IL-2 in MLV. In this test, 7 groups of BALB/c mice were injected in the footpad with $10^5$ C26 colon carcinoma cells. Seven days later, 8 mg/kg free or liposomal adriamycin was administered i.v. Free or liposomal IL-2, as shown in Table IV, was administered i.p. according to the schedule described above. Results are shown in Table IV.

TABLE IV

| GROUP | TREATMENT | NUMBER OF TUMOR FREE MICE, DAY 30 | NUMBER OF TUMOR FREE MICE, DAY 65 |
|---|---|---|---|
| 1 | Control | 0/7 | 0/7 |
| 2 | ADR | 0/7 | 0/7 |
| 3 | ADR/free IL-2 | 0/7 | 0/7 |
| 4 | ADR/MLV-IL-2 | 1/8 | 0/8 |
| 5 | DOXIL ® | 4/8 | 102 |
| 6 | DOXIL ®/free IL-2 | 3/8 | 2/8 |
| 7 | DOXIL ®/MLV-IL-2 | 6/8 | 4/8 |

As the data shows, administration of liposomal drug alone was somewhat beneficial, but only the group receiving the combined liposomal treatment showed significant recovery from tumors. In this group (group 7), it was also observed that the tumors were significantly smaller than in the other groups.

IV. Administration

For use in humans, a therapeutically effective dose of the composition typically corresponds to 20–100 mg adriamycin/m² of body surface. For IL-2, a preferred dose corresponds to 50,000–500,000 CU per square meter of body surface. Administration may be by intraperitoneal (ip), subcutaneous (sc), intravenous (iv), intraarterial (ia), or intramuscular (im) injection. Liposomes in the form of large multilamellar vesicles (MLV's) are preferred for intraperitoneal, subcutaneous or intramuscular administration, while SUV's are preferred for intravenous as well as intramuscular administration.

As shown above, administration of liposome-encapsulated chemotherapeutic drug is followed by administration of the liposome-encapsulated cytokine. While specific time intervals and courses of treatment have been shown in the examples above, it is understood that dosages, time intervals between courses, and the number of courses of treatment, for both drug and cytokine, may be varied depending on the extent of symptoms and the condition of the patient.

While the invention has been described with reference to specific methods and embodiments, it will be appreciated that various modifications may be made without departing from the invention.

What is claimed is:

1. A method for antitumor therapy, comprising
administering to a subject in need of such treatment, a therapeutically effective amount of a non-encapsulated chemotherapy drug and an immunostimulating cytokine,
wherein the cytokine is encapsulated in multilamellar liposomes (MLV),
said treatment being characterized in that the subject is administered on non-consecutive days with two or more DOSES of said liposome encapsulated cytokine,
a first dose being administered at least 3 days following administration of said chemotherapeutic drug,
wherein the time between administrations is such that the therapeutic effect of the combined administrations is greater than the sum of the therapeutic effects produced by administration of said chemotherapeutic drug alone and by administration of said immunostimulating cytokine alone.

2. The method of claim 1, wherein said cytokine is selected from the group consisting of interleukin-2 (IL-2), IL-12, IL-15, IL-18, INF-γ, INF-α, INF-β, G-CSF, and GM-CSF.

3. The method of claim 2, wherein said cytokine is IL-2.

4. The method of claim 1, wherein the liposomes comprise at least one lipid selected from the group consisting of dimyristoyl phosphatidyl choline (DMPC), dimyristoyl phosphatidyl glycerol (DMPG), 1,2-distearoyl-3-trimethylammonium propane (DSTAP), phosphatidyl choline, phosphatidyl ethanolamine and cholesterol.

5. The method of claim 4, wherein said cytokine is encapsulated in liposomes comprising (1) DMPC and (2) at least one additional lipid selected from the group consisting of dimyristoyl phosphatidyl glycerol (DMPG), and 1,2-distearoyl-3-trimethylammonium propane (DSTAP), said at least one additional lipid being in an amount of up to 50%.

6. The method of claim 5, wherein said liposome is composed of DMPC and DMPG.

7. The method of claim 6, wherein the liposome comprise DMPC and DMPG in a molar ratio of about 9:1.

8. The method of claim 1, wherein said chemotherapeutic drug is selected from the group consisting of a chemotherapeutic anthraquinone, cisplatin, and a topoisomerase I inhibitor.

9. The method of claim 8, wherein said chemotherapeutic drug is doxorubicin (adriamycin).

10. A method for antitumor therapy, comprising
administering to a subject in need of such treatment, a therapeutically effective amount of a chemotherapeutic drug encapsulated in liposomes and an immunostimulating cytokine encapsulated in MLV,
said treatment being characterized in that the subject is administered on non-consecutive days with two or more doses of said MLV encapsulated cytokine,
a first dose of said MLV encapsulated cytokine being administered at least 3 days following administration of said liposome encapsulated chemotherapeutic drug,
wherein the time between administration of said MLV encapsulated chemotherapeutic drug and said liposome encapsulated cytokine is such that the combined therapeutic effect of said administrations is greater than a sum of the therapeutic effect produced by administration of the liposome encapsulated chemotherapeutic drug alone by administration of said MLV encapsulated immunostimulating cytokine alone.

11. The method of claim 10, wherein said cytokine is selected from the group consisting of interleukin-2 (IL-2), IL-12, IL-15, IL-18, INF-γ, INF-α, INF-β, G-CSF, and GM-CSF.

12. The method of claim 11, wherein said cytokine is IL-2.

13. The method of claim 10, wherein the MLV encapsulating said immunostimulating cytokine comprise at least one lipid selected from the group consisting DMPC, DMPG, DSTAP, phosphatidyl choline, phosphatidyl ethanolamine and cholesterol.

14. The method of claim 13, wherein said cytokine is encapsulated in MLV comprising (1) DMPC and (2) at least one additional lipid selected from the group consisting of DMPG and DSTAP, said at least one additional lipid being in an amount of up to 50%.

15. The method of claim 14, wherein said MLV comprise of DMPC and DMPG.

16. The method of claim 15, wherein the MLV DMPC and DMPG are present in a molar ratio of about 9:1.

17. The method of claim 10, wherein the liposomes encapsulating said chemotherapeutic drug comprise 1–10 mole percent of a lipid having a polar head group dericatized with a polyethylene glycol chain which has a molecular weight of between 750 and 10,000 dalton.

18. The method of claim 10, wherein said chemotherapeutic drug is selected from the group consisting of a chemotherapeutic anthraquinone, cisplatin, and a topoisomerase I inhibitor.

19. The method of claim 18, wherein said chemotherapeutic drug is doxorubicin (adriamycin).

20. The method of claim 19, wherein said chemotherapeutic drug is polyethylene glycol-coated liposomal doxorubicin.

* * * * *